United States Patent
Jelic

(10) Patent No.: US 6,596,009 B1
(45) Date of Patent: Jul. 22, 2003

(54) RETRIEVABLE ENDOSCOPIC ORBITAL FLOOR SPLINT

(76) Inventor: Jeffrey Jelic, Box 967, Chapel Hill, NC (US) 27514

( * ) Notice: Subject to any disclaimer, the term of this patent is extended or adjusted under 35 U.S.C. 154(b) by 216 days.

(21) Appl. No.: 09/627,087

(22) Filed: Jul. 27, 2000

Related U.S. Application Data

(60) Provisional application No. 60/146,031, filed on Jul. 28, 1999.

(51) Int. Cl.⁷ ............................................. A61M 29/00
(52) U.S. Cl. .................... 606/191; 606/60; 606/196; 623/10
(58) Field of Search ................. 606/60, 191, 196, 606/197, 199, 151; 623/17.18, 17.19, 10

(56) References Cited

U.S. PATENT DOCUMENTS

| | | | |
|---|---|---|---|
| 3,800,788 A | | 4/1974 | White ........................ 128/83 |
| 4,414,977 A | * | 11/1983 | Rezakhany ................. 606/199 |
| 4,778,466 A | * | 10/1988 | Brotman ..................... 623/10 |
| 5,104,401 A | * | 4/1992 | Kurz ........................... 623/10 |
| 6,096,079 A | * | 8/2000 | Eaton ...................... 623/17.18 |

OTHER PUBLICATIONS

Fonseca, Raymond J, et al., Management of Head and Neck Injuries, Oral and Maxillofacial Trauma, Copyright 1997, pp. 480–495, Second Edition, vol. 1, W.B. Saunders Company, Philadelphia, Pennsylvania.

Hauser, Michael S., Management of Ocular and Orbital Trauma, Oral and Maxillofacial Surgery, Copyright 1992, pp. 529–531, vol. 1, J.B. Lippincott Company, Philadelphia, Pennsylvania.

Rowe, N.L., Fractures of the Zygomatic Complex and Orbit, Maxillofacial Injuries, 1985, pp. 435–437, 439, 505–510, vol. 1, Churchill Livingstone, Medical Division of Longman Group Limited, Great Britain.

* cited by examiner

Primary Examiner—Julian W. Woo
(74) Attorney, Agent, or Firm—Christie, Parker & Hale, LLP

(57) ABSTRACT

A endoscopic orbital floor splint for placement in a maxillary sinus for supporting an orbital floor having a pedicle portion with an upper surface and lower surface, and a support portion extending below the lower surface of the pedicle portion which is adapted to force pedicle portion upwardly to support the orbital floor. The pedicle portion can be generally triangular shaped with rounded corners and an inferior optical nerve notch formed on one side thereof, and the support portion can be generally ring-shaped or be an elongate leg shape. Optionally, a neck can be provided between the pedicle portion and the support portion. The endoscopic orbital floor splint is formed of biocompatible flexible and resilient material, such as silicone rubber.

30 Claims, 4 Drawing Sheets

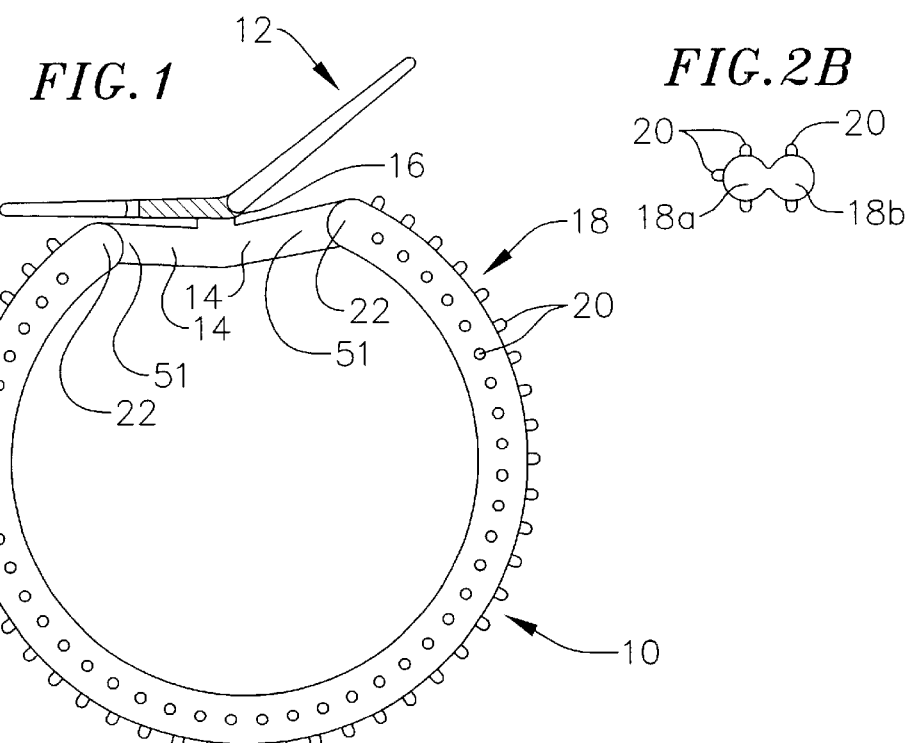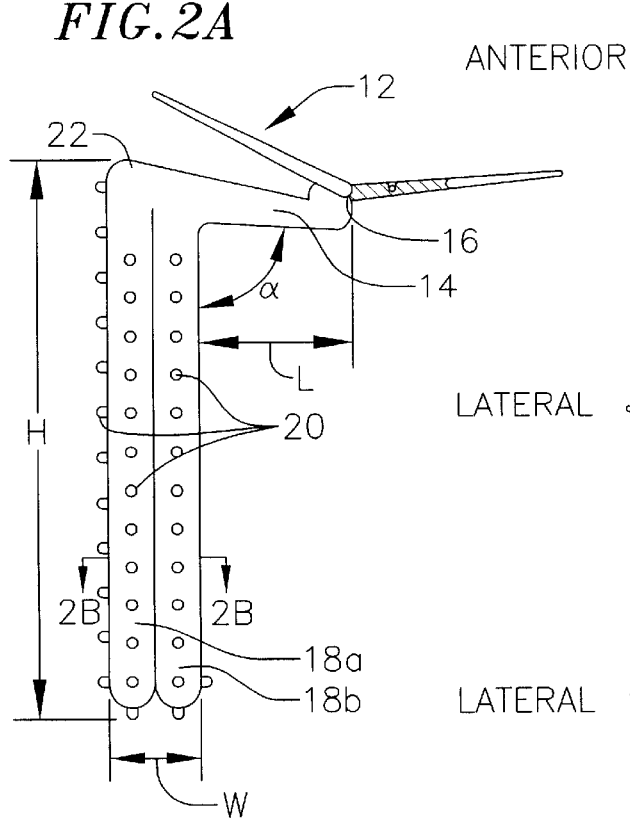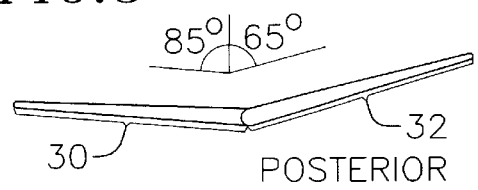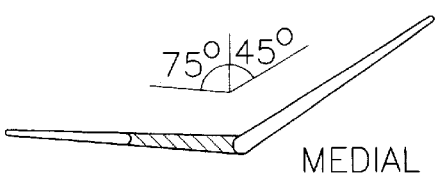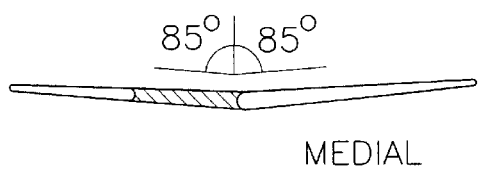

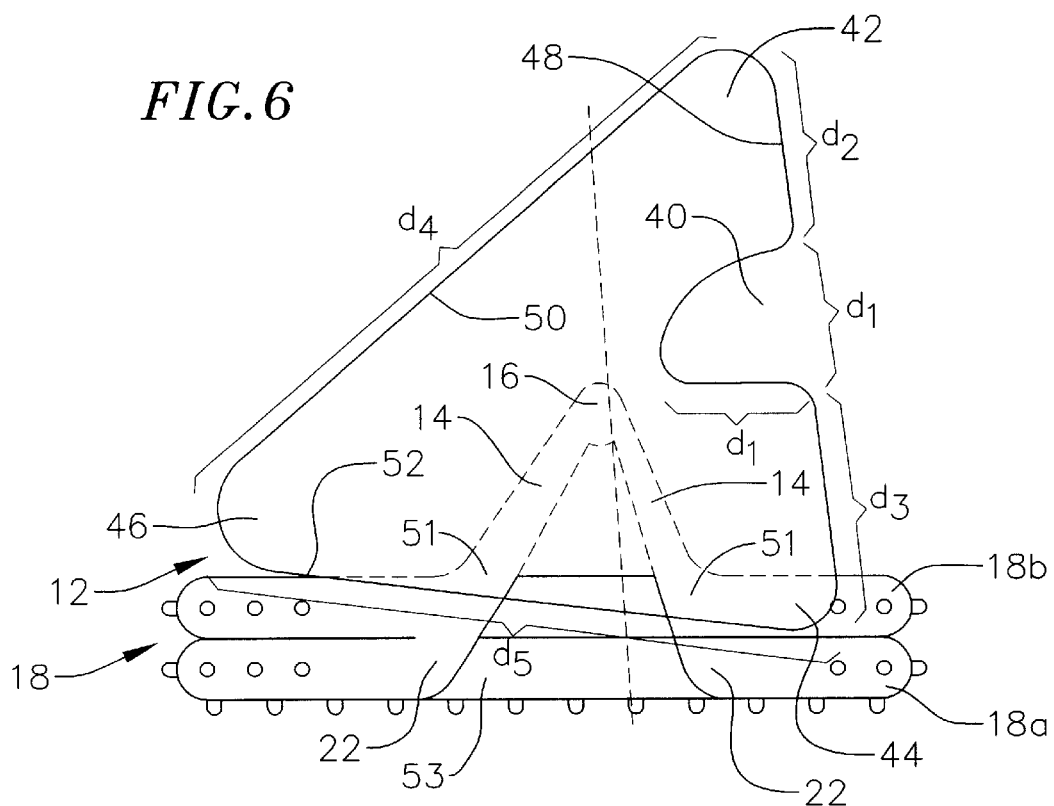
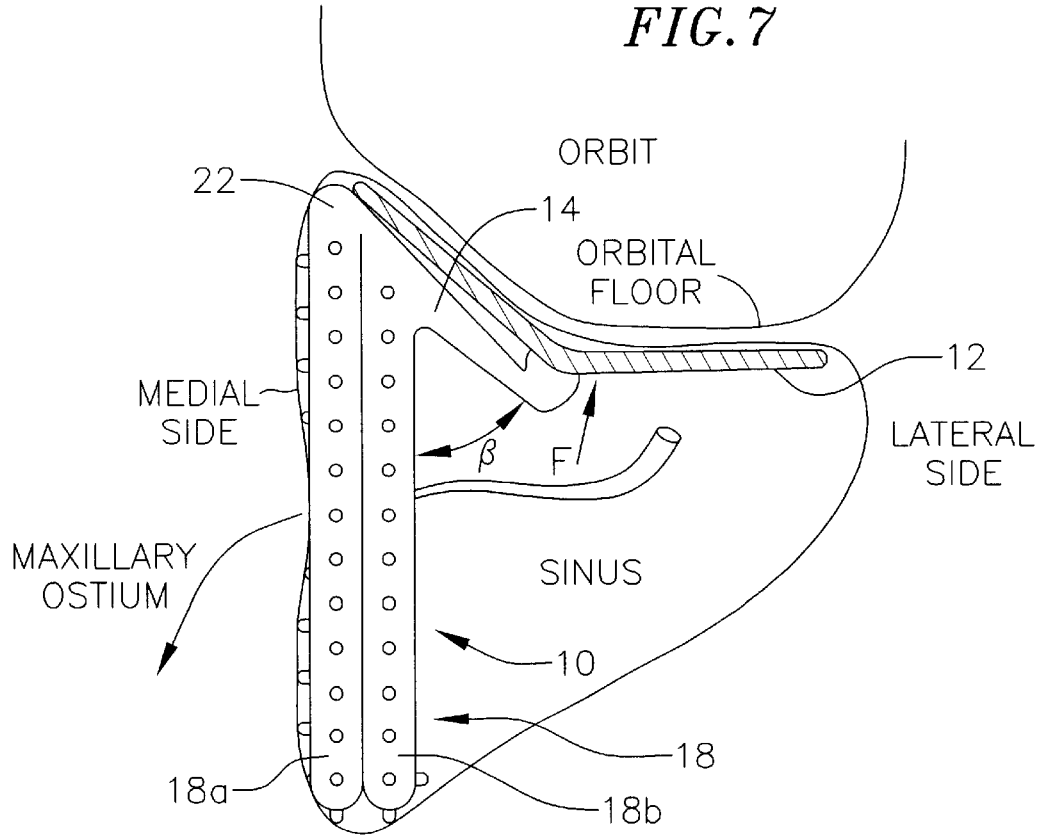

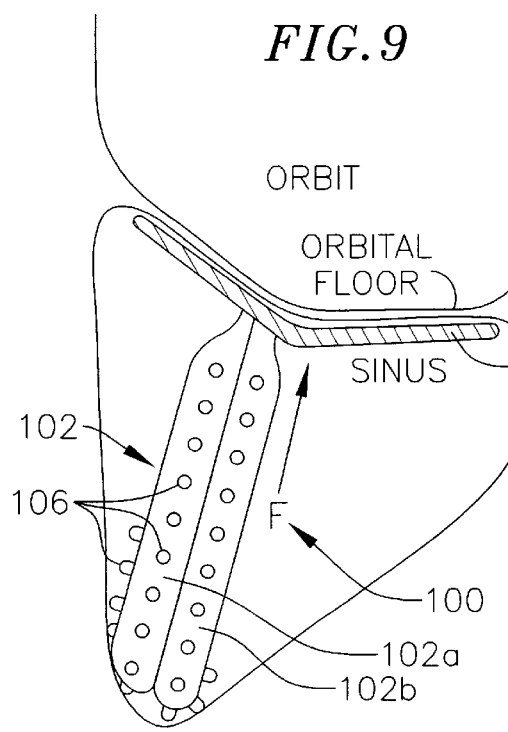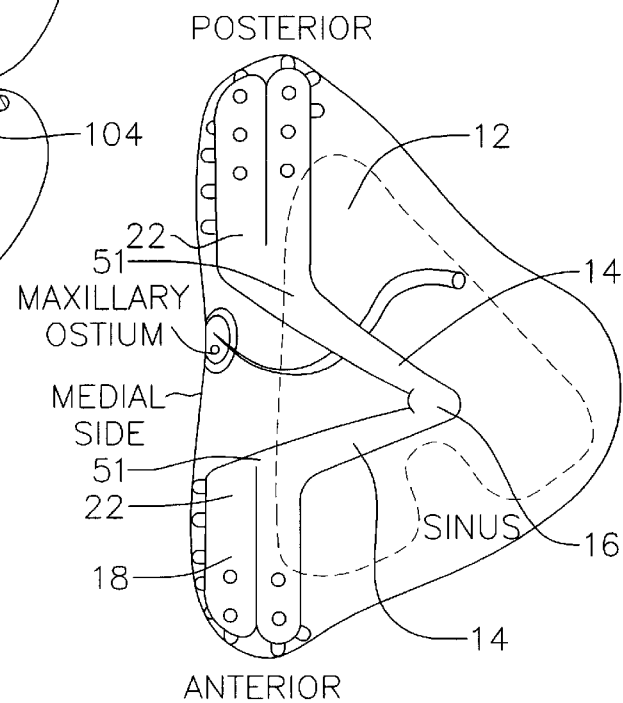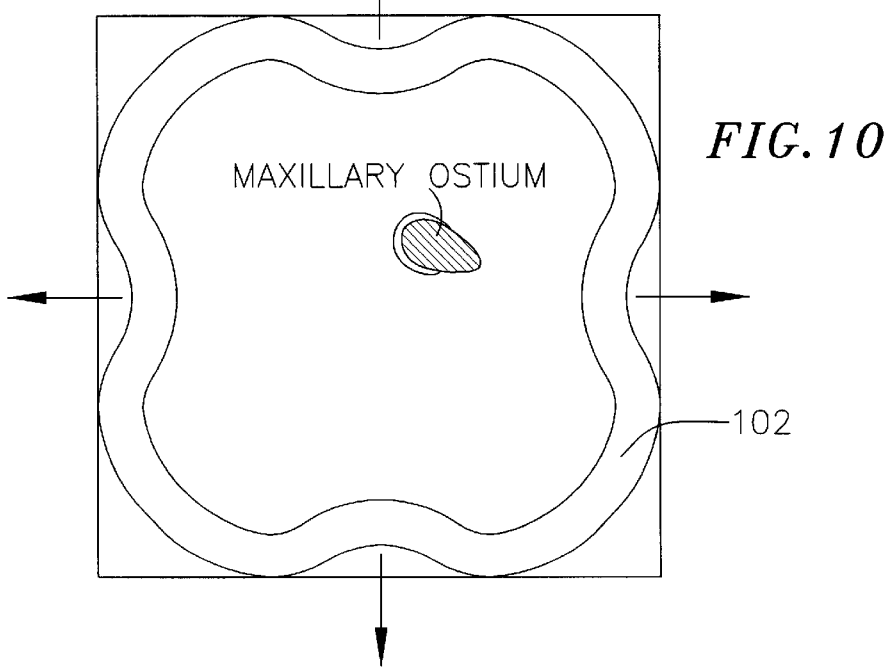

RETRIEVABLE ENDOSCOPIC ORBITAL FLOOR SPLINT

CROSS-REFERENCE TO RELATED APPLICATION(S)

This application claims priority based upon provisional patent application No. 60/146,031, filed Jul. 28, 1999.

BACKGROUND OF THE INVENTION

Fractures of the orbital floor of the eye socket, particularly blow out fractures, can be difficult to diagnose, and if not promptly repaired, can result in diplopia, mismatching of the ocular level between the patient's two eyes, long term damage to the ocular nerve eye, and other conditions that cannot always be repaired by subsequent surgeries.

The orbit (eye socket) can be conceptualized as a four walled cone shaped vault. The peripheral portions of this vault (orbital rim, orbital apex and the most lateral aspect of the orbital floor) are fairly rigid and somewhat resistant to fracture. The internal portion of the orbital vault is constructed of bone analogous to a very thin egg shell (averaging 0.27 mm thick). The thinnest and weakest portions are the inferior(floor) and medial walls of the orbit.

Fractures of the orbital floor classically occur by two mechanisms. The first is called an orbital "blow out fracture". Blow out fractures occur when kinetic energy is delivered to the globe (eye ball) in a discrete fashion. Examples could include a fist or baseball. Such a direct blow to the globe drives the globe into orbit like a piston. The hydraulic pressure is distributed within the cone shaped walls of the orbit and causes the weakest wall to fracture and rapidly decompresses the orbit. Since the weakest wall is the orbital floor, these bones fracture, and then blow out (swing inferiorly) in a trap door fashion, from periosteal hinges. This allows the contents of the orbit (periorbital fat, extraoccular muscles, and globe) to descend into the maxillary sinus below.

The second classic mechanism for orbital floor fracture is as a component to fractures of the zygomatic-maxillary complex (cheek bone or ZMC) fractures. In these cases, kinetic energy is delivered to the malar prominence of the zygoma (cheek bone) and the zygoma is driven into the maxillary sinus. The zygoma is a very thick bone that composes the lateral and inferior-lateral portions of the orbital vault. The rigid zygoma rarely fractures but the thin orbital floor, which is attached to it, buckles and shatters.

Symptoms of fractures involving the orbital floor may include 1) inability to gaze superiorly due to the tethering effect of entrapped fat and/or extraoccular muscles on the edges of fractured bone, 2) diplopia (double vision) due to either disruption of the extraoccular muscle function which coordinates binocular vision as described above, or altered pupillary alignment, 3) enophthalamos (retruded and unequal pupil levels) as the globe sags when the supporting periorbital fat herniates into the maxillary sinus and, finally, 4) paresthesia or anesthesia of the affected cheek. Since the inferior orbital nerve (the sensory nerve to the cheek) travels in a groove in the orbital floor/roof of maxillary sinus, direct injury from bone fragments or tension from sagging orbital contents disrupts normal nerve function.

To correct visual and aesthetic defects associated with orbital floor fractures, the volume of the periorbital soft tissue, and the volume of the boney vault must be equilibrated. Periorbital fat and muscles must be relocated back into the orbit and the integrity of the orbital vault must be restored. The fractured bone of the orbital floor must then be stabilized long enough for osteosynthesis to occur (approximately 4–6 weeks). The difficulty with repairing the orbital floor has to do largely with the difficulty to stabilize these paper thin bones, against the weight of the intra orbital contents, long enough for osteosynthesis to occur.

Methods typically employed in the repair of maxillofacial fractures do not work within the orbit. Even if a surgical approach allowed placement of wires, screws or bone plates, the bones are too thin and simply break into smaller pieces.

Traditional repairs of the orbital floor therefore have approached the problem from two avenues. The first method is from the orbit. This approach requires either a subciliary skin incision (2 mm below the lower eyelashes), or a transconjunctival incision (inside the eye lid) and then dissecting through the tissues of the lower eye lid to expose the fracture from the superior surface. Herniated tissue is then raised out of the maxillary sinus and the integrity of the orbital floor is restored by placing a thin implant over the hole in the floor. The implant rests on the stable peripheral edges of the fracture-analogous to a sheet of plywood temporarily placed to cover a hole in a floor. Theoretically, the best implant for the job would be autogenous cortical bone. The graft would eventually incorporate and the risk for long term complications would essentially be eliminated. In reality, such implants are often much thicker than required and do not conform to the true shape of the orbital floor. These drawbacks often prevent the implant from achieving the volumetric balance necessary for proper aesthetics and function of the globe.

Additionally, there are initial infectious risks with non stabilized bone and there is also risk of associated donor site morbidity. Alloplastic materials are by far the most common implants used to repair orbital floor fractures. Silicon sheeting, polytetrafluoroethylene (Teflon®), polyethylene, Gelfilm™, Marlex™ mesh, hydroxyapatite, methyl methacrylate and titanium mesh are a few examples.

Titanium mesh has the advantage that it may be rigidly fixed to the inferior orbital rim and therefore has less risk of infection or extrusion, and can be used when the blowout fracture is so large that stable margins are not available upon which to rest the implant. However, titanium mesh is costly, requires significantly more skill and experience to shape and place into proper position, will tether the globe if placed incorrectly, and will complicate radiologic exams postoperatively. All of the other materials are less expensive, easy to shape, easy to place, and have minimal interference with the function of the globe. But since all of the latter materials are placed passively over the fracture, and never become integrated therewith, migration, extrusion and infection become lifelong risks. It is important to note that due to the juxtaposition of these anatomic structures, any sinus infection can easily become an intraorbital infection and in a worse case scenario, an intracranial infection. Therefore, although such infections are not frequent, they can be quite serious.

Finally, all the approaches that utilize surgical dissections through the lower eye lid carry the potential sequela of a visible scar, ectropion or entropion (lower lid margin rolled outwardly or inwardly, respectively), infection, injury to neuro vascular structures, the tear duct aperatus, and to the extraoccular muscles of the globe, as well as retrobulbar hematoma and very rarely blindness.

To avoid the short and long term complications of the orbital exposure, surgeons have developed a second method and approach the orbital floor from the maxillary sinus.

Since the orbital floor is also the roof of the maxillary sinus, orbital floor fractures can be exposed by making an antrostomy in the anterior maxilla just above the roots of the maxillary teeth. This approach simply requires an incision in the gingiva and removing the paper thin bone of the anterior maxilla between the zygomatic buttress and piriform rim. In cases of blowout fractures, the fractured bones and periorbital fat can be observed herniating down through an opening in the sinus roof. The orbital contents can be pushed back into the orbit from below and then the bone fragments can be aligned into proper position. Once again, the difficulty with stabilization of the bone fragments long enough for osteosynthesis is the pivotal issue. Without stabilization, gravity will pull the orbital contents back into the sinus.

Surgeons have classically employed two methods to stabilize the reduced fragments from the intrantral (antrum=sinus) approach. The oldest method is to systematically layer iodoform gauze within the sinus. The gauze will completely occlude the sinus and the bone fragments cannot be displaced inferiorly. A small intranasal antrostomy (antral=sinus; ostomy=hole) is produced and the tail of the gauze extrudes into the nares or through the maxillary gingiva underneath the upper lip. This "tail" will be used to retrieve the gauze 4–6 weeks later. The second, more modern version of this technique is to place a foley balloon into the sinus and then fill the bladder with saline. As the balloon expands it tamponades the sinus and eventually places pressure up against the fractured bone in order to keep the orbital contents from reherniating into the sinus. The "retrieval tail" in this case, is the valve from which the balloon is filled, and it is also sutured in a position sticking out through the nares or buccal vestibule.

While the transantral approach eliminates the risk of the orbital approach, it is not without shortcomings. First, the pressure within the sinus mimics the symptoms of severe sinus disease and may be quite uncomfortable for the patient. Second, the sinus is packed completely full for 4–6 weeks. The respiratory mucous that lines the maxillary sinus however, continues to produce its normal secretions despite not having an outlet. Compounding this problem is the fact that the cilia of the respiratory mucous, which normally propel secretions and bacteria in a coordinated fashion out of the maxillary sinus via the maxillary ostium, are also unable to function. The combination causes stagnation and bacterial overgrowth. Odor and infection then become a problem. Additionally, pressure from the packing can induce permanent damage to the delicate respiratory mucosa and result in the same histologic changes seen with chronic sinus disease. Third, the bones are rarely anatomically reduced. In the case of iodoform gauze, over time, the iodoform gauze tends to settle and retract from the sinus roof/orbital floor. This reduces the pressure on the fractured bones and allows a variable degree of relapse to the herniation intraorbital tissues. Fourth, the packing material must be retrieved. If the gauze ribbon is not layered correctly, or if the gauze is removed too quickly, knots may be created within the sinus. If this occurs, to remove the "bird's nest" the sinus must be opened wide enough to cut the gauze free.

The saline balloon is much easier to place and much easier to remove and will not settle over time. The balloon, however, does not conform very well against the walls of the irregular pyramid shape of the sinus. Therefore, an anatomic reduction and fixation of the fracture rarely occurs. Also, the saline balloon does not eliminate any of the problems discussed in describing the gauze technique and the relatively large valve protruding through the nose or through the gingiva beneath the upper lip which can be unsettling and a nuisance to the patient. Present transantral supports clearly have drawbacks.

A discussion of the management of orbital floor fractures must address the issue of "no treatment". Because a satisfactory modality for the treatment of orbital floor fractures has not been developed, the cure of the pathology has often times not been worth the risk. This realization has created a search for the radiological and/or clinical examination criteria that will separate those fractures that will not develop visual and aesthetic complications, from those fractures that will develop visual and aesthetic complications and therefore warrant the potential complications of surgery. Conservative criteria typically expressed in specialist journals advise, in the asymptomatic patient, that the surgeon should wait at least 10–14 days to see if any symptoms warranting surgery develop. 10–14 days is chosen because this is the time necessary for traumatic edema to resolve and unmask the degree of periorbital fat herniation. The sooner the fracture is operated upon, the more likely a satisfactory post operative result will be achieved. Waiting 14 days allows periorbital fat necrosis and scar bands to form, and may compromise even the most perfect operative repair.

There accordingly remains a need for a better implant and method for repairing blow out fractures of the orbit.

SUMMARY OF THE INVENTION

The invention provides a retrievable endoscopic orbital floor splint that is formed from a biocompatible material, such as synthetic rubber including silicone rubber, that is insertable and retrievable through the maxillary sinus.

In one embodiment, the retrievable endoscopic orbital floor splint includes a pedicle portion with an upper surface and a lower surface (wherein the upper surface is adapted to impinge on the underside of the orbital floor), and a support extending from the lower surface of the pedicle portion for retaining the pedicle portion in place in the maxillary sinus pressed up on the orbital floor until it is removed.

In another embodiment, the retrievable endoscopic orbital floor splint can comprise a knobbed and generally ring-shaped support with a somewhat thin, curved pedicle attached to one portion of the ring. The ring portion can be placed along the medial wall of the maxillary sinus (the widest dimension of the sinus), and is stabilized by the recesses that are formed by the junction of the anterior wall of the maxillary sinus with the medial wall of the maxillary sinus, and the posterior wall of the maxillary sinus with the medial wall of the maxillary sinus. When properly sized (i.e. pediatric and small, medium, and large adult sizes) and located, the ring will be slightly compressed. The deformation in the ring portion will provide the potential kinetic energy necessary to prevent the intraorbital contents from herniating into the sinus.

In yet another embodiment of the retrievable endoscopic orbital floor splint can comprise a pedicle portion with an elongate and flexible leg portion extending from an underside thereof, which leg portion can be flexed and fit into the maxillary sinus, and can also be cut and shortened to better fit into the maxillary sinus.

In the various embodiments, the pedicle portion can have a variety of shapes, such as a roughly triangular and cupped shape. A notch can be formed on one side edge of the pedicle portion to avoid a side edge of the pedicle from possibly impinging on the infraorbital nerve.

BRIEF DESCRIPTION OF THE DRAWINGS

The invention is best described with reference to the drawings, as follows:

FIG. 1. is a side view of an embodiment of the retrievable endoscopic orbital floor splint that has a cup-shaped pedicle portion, a neck extending from an underside of the pedicle portion, and generally ring-shaped support attached to the neck.

FIG. 2A is an anterior view of the retrievable endoscopic orbital floor splint of FIG. 1.

FIG. 2B is a cross-sectional view through view lines 2B—2B of FIG. 2A.

FIG. 3 is a side view showing the anterior-posterior angulation of the pedicle portion of the retrievable endoscopic orbital floor splint of FIG. 1.

FIG. 4 is a side view showing the posterior 2/3 of the medial to lateral angulation of the pedicle portion of the retrievable endoscopic orbital floor splint of FIG. 1.

FIG. 5 is a side view showing the anterior 1/3 of the medial to lateral angulation of the pedicle portion of the retrievable endoscopic orbital floor splint of FIG. 1.

FIG. 6 is superior to inferior view of the retrievable endoscopic orbital floor splint of FIG. 1.

FIG. 7 is an anterior to posterior view of the retrievable endoscopic orbital floor splint of the invention of FIG. 1 in place in sinus and supporting the orbital floor.

FIG. 8 is a view of the retrievable endoscopic orbital floor splint of FIG. 1 in the sinus viewed from above looking inferiorly (with the pedicle shown in phantom lines.)

FIG. 9 is an anterior to posterior view of another embodiment of the retrievable endoscopic orbital floor splint of the invention without a neck between the ring-shaped support and the pedicle portion.

FIG. 10 is a diagrammatic view showing how the ring-shaped support of the retrievable endoscopic orbital floor splint (shown without the pedicle portion) of the invention of FIGS. 1 and 9 is compressed into the maxillary sinus and exerts potential kinetic energy to elevate the orbital floor in a patient.

DETAILED DESCRIPTION OF THE INVENTION

Figure 11:
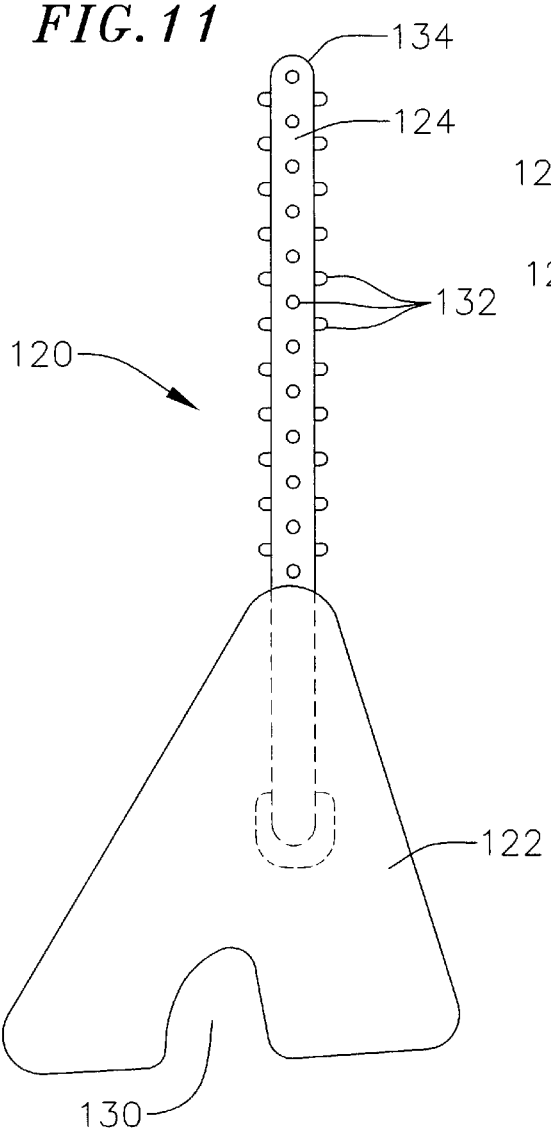
FIG. 11 is a top plan view showing another embodiment of the retrievable endoscopic orbital floor splint of the invention having a pedicle portion and a flexible leg portion extending from a bottom of the pedicle portion.
Figure 12:
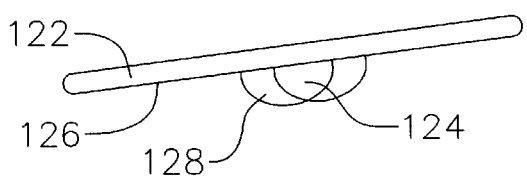
FIG. 12 is a front view of the retrievable endoscopic orbital floor splint of FIG. 11.

FIG. 1. is a side view of a first embodiment of the retrievable endoscopic orbital floor splint 10 that has a pedicle portion 12, a neck 14 extending from an underside 16 of pedicle portion 12, and a generally ring-shaped support 18 extending downwardly from neck 14 from upper regions 22 thereof. A plurality of small protrusions or knobs 20 are optionally located on outer surfaces of ring-shaped support 18, the purpose of which will be described further below. The retrievable endoscopic orbital floor splint 10 is preferably formed from a bio-compatible, flexible and resilient material, such as silicone rubber or other polymers. Pedicle portion 10 can preferably be cup-shaped to better fit the shape of the underside of the orbit.

FIG. 2A is an anterior view of retrievable endoscopic orbital floor splint 10. As can be seen, ring-shaped support 18 can be formed in a double tube construction 18a and 18b (where the double tubes are preferable formed together, as best shown in FIG. 2B.) This construction helps to prevent any tendency of the generally ring-shaped support 18 to laterally bend into an "S" shape. Neck 14 extends from an upper region 22 of ring-shaped support 18 at angle α and is fixed to underside 16 of pedicle portion 12. Angle α is preferably 60° or more to provide for flexion between pedicle portion 12 and ring-shaped support 18. As an example of the dimensions of the retrievable endoscopic orbital floor splint 10, the ring-shaped support 18 can have a height H of 30 mm and a width W of 5 mm for the double tubes 18a and 18b. Neck 14 can be of a desired length L, such as about 7 mm, although other dimensions can be used for different patient requirements (e.g. infant, adolescents, small and large adults, etc.) Sized as such, when the support 18 is placed adjacent to the medial antral wall, the neck attachment point 16 will thereby be spaced about 12 mm from the medial antral wall (L+W=7 mm+5 mm.)

FIG. 3 is a side view showing the anterior-posterior angulation of the posterior 2/3 of pedicle portion 12. The anterior section 30 (sized at about 10 mm) is relatively flat with about a 5° anterior elevation from horizontal (or 85° from the vertical.) The posterior 20 mm section 32 is preferably steadily inclined superiorly at approximately 35° from horizontal (or 65° from the vertical.)

Turning to FIG. 4. there is shown a side view of the posterior 2/3 of the medial to lateral angulation of the pedicle portion 12. The posterior most 20 mm of the medial side (measuring about 12 mm) is angled superiorly at approximately 45° from the vertical plane, and the lateral 12 mm is angled superiorly at approximately 15° from the horizontal plane (75° from the vertical plane.)

Referring to FIG. 5, there is shown a side view of the posterior 1/3 of the medial to lateral angulation of the pedicle portion 12. The lateral and medial sides are both lifted up by about 5° from the horizontal plane (85° from the vertical plane.)

Turning to FIG. 6, there is shown a superior to inferior view of the retrievable endoscopic orbital floor splint 10. As can be seen, pedicle portion 12 has a generally triangular shape with rounded corners. As noted above, it is also somewhat cup shaped. A notch 40 for the inferior orbital nerve is formed on an anterior side 48 of pedicle portion 12. Notch 40 can have a width $d_1$ of about 6 mm, and the distance $d_2$ from anterior corner 42 of pedicle portion to notch 40 can be about 6 mm, and the distance $d_3$ from notch 40 to anterior corner 44 can be about 7 mm, for a total anterior side length of about 25 mm. The distance $d_4$ of the posterior side edge 50 from posterior corner 46 to anterior corner 42 can be about 30 mm and distance $d_5$ of the medial edge 52 from posterior corner 46 to anterior corner 44 can be about 24 mm. Pedicle portion 12 is thus roughly triangular with dimensions of 30 mm×25 mm×24 mm, with a 6 mm wide ($d_1$) by 8 mm deep ($d_6$) notch 40 in anterior edge 48 of pedicle portion 48. Pedicle portion 12 may smooth (as shown), knobbed or perforated with 1 mm holes (not shown.) As also can be seen, neck portion 14 has a generally V-shape with two ends 51 merging with the two spaced apart upper regions 22 of ring-shaped support 18 and two sections merging at an apex at attachment point 16 on an underside of pedicle portion 12. Neck 14 extends outwardly from a plane passing through support 18. The attachment point 16 is near a center point of the triangular shaped pedicle portion 12. Ring-shaped support 18 has an opening 53 between spaced apart upper regions 22 where neck 14 is located.

FIG. 7 is an anterior to posterior view of retrievable endoscopic orbital floor splint 10 in place in sinus and supporting the orbital floor. As can be seen, when placed into the maxillary sinus, retrievable endoscopic orbital floor splint 10 will have ring-shaped support 18 will be close to the medial side of the sinus cavity. The protrusions 20 will help prevent the sides of the ring-shaped support 18 from making too tight and forceful contact with the medial side of the maxillary sinus and thereby act to prevent damage to the cilia lining the maxillary sinus and help prevent scraping of the mucus coated sinus cavity. Ring-shaped support 18 allows fluid to be drained as normal from the maxillary ostium. Neck 14 has flexibility and resilience as does pedicle portion 12, and will flex down from its resting angle α of FIG. 2 to a smaller angle β to cause force F to be applied to the pedicle portion 12 and thus to the orbital floor. The resilience of retrievable endoscopic orbital floor splint 10 will cause the upper surface of pedicle portion 12 to push up on and support the orbital floor. Indeed, the cupped pedicle portion 12 will flex as required to closely conform to the orbital floor.

FIG. 8 is a view of the retrievable endoscopic orbital floor splint 10 in the sinus viewed from above looking inferiorly (with the pedicle portion 12 shown in phantom lines for ease of view.) Neck 14 and its attachment point 16 to pedicle portion 12 is shown, as well as clearance for drainage via the maxillary ostium.

FIG. 9 is an anterior to posterior view of another embodiment of the retrievable endoscopic orbital floor splint 100 of the invention, but without a neck located between a ring-shaped support 102 and a pedicle portion 104. Pedicle portion 104 can be sized and shaped as with the first embodiment shown and described above and in FIGS. 1–8. Ring-shaped support 102 will not have a neck region, but can have protrusions 106 formed thereon, and can have a double tube construction 102a and 102b. As shown, when placed in the maxillary sinus, ring-shaped support 102 will not ride against the medial side of the maxillary sinus, but as a whole will deflect and conform as necessary exert force F on the orbital floor.

FIG. 10 is a diagrammatic view showing how the ring-shaped support 102 of the retrievable endoscopic orbital floor splints 100 (shown without the pedicle portion) of the invention of FIG. 9, is compressed to fit into the maxillary sinus and exert potential kinetic energy to elevate the orbital floor of the patient. The preferred design of a double ring 102a and 102b will help eliminate lateral "S" bends, and only allows central bends to create potential kinetic energy to elevate the orbital floor position. (The ring-shaped supports 18 and 102 can also have a generally toroid shape.) The unblocked position of the maxillary ostium is shown. This same mechanics will be apparent in the embodiment of the ring-shaped support 18 of the first embodiment of FIG. 1.

Figure 14:
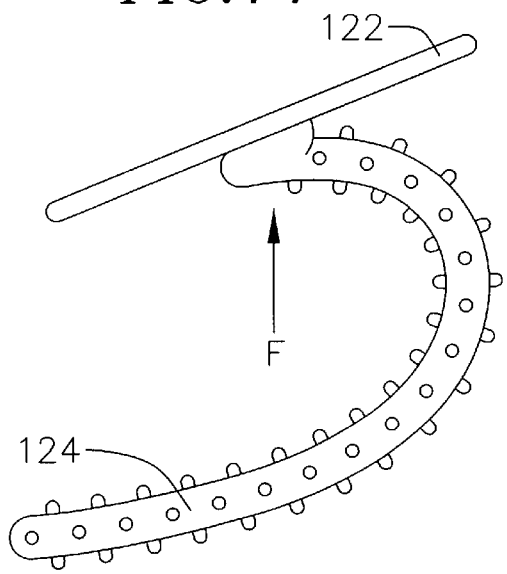
FIG. 14 is a side view of the retrievable endoscopic orbital floor splint of FIG. 11, but with its leg portion flexed, as it would be when inserted into the maxillary sinus.
Figure 13:
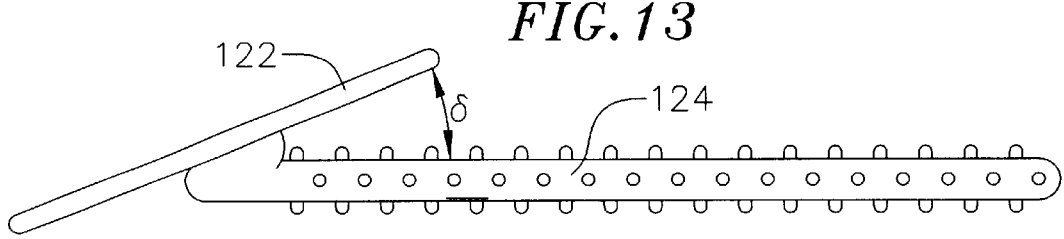
FIG. 13 is a side view of the retrievable endoscopic orbital floor splint of FIG. 11.

FIGS. 11–14 are various views of a third embodiment of the retrievable endoscopic orbital floor splint 120 of the invention. It has a pedicle portion 122 and a flexible and resilient leg portion 124 affixed Lo a bottom 126 at an attachment region 128. Leg portion 124 extends laterally outwardly from pedicle portion 122 at an angle δ from pedicle portion 122. Angle δ can be varied as desired, but can be from 0° to 90°, and more preferably from 10° to 30°. In its normal resting position, prior to it being positioned within the maxillary sinus, leg portion 124 can be relatively straight. Retrievable endoscopic orbital floor splint 120 is preferably formed from bio-compatible material, such as silicone rubber or other polymers that is flexible and resilient. Retrievable endoscopic orbital floor splint 120 can be formed as a unitary structure by molding as a single piece, or can be glued or welded together. Pedicle portion 122 is preferably cupped and can have similar qualities as described with reference to the embodiments of FIGS. 1–10, namely, it can have a generally triangular shape with rounded corners, and can have a notch 130 for the inferior orbital nerve to prevent pedicle portion 122 from impinging thereon. Leg portion 124 can be provided with protrusions 132 to prevent continuous and complete contact of leg portion 124 with the cilia lining the inside of the maxillary sinus. Leg portion 124 should have a length sufficient such that when it is flexed downwardly and inwardly as shown in FIG. 14, it will exert an upward force F on pedicle portion 122. For greater versatility, leg portion 124 can be sized to be relatively long (e.g. 70 mm or longer) and can be cut to a desired length at end 134 by the surgeon prior to localization in the maxillary sinus.

Having described the various embodiments of the invention, its use, placement in a patient, and operation will now be described.

The ideal approach to orbital floor fractures should incorporate the following features and advantages: 1) expose the fracture from the maxillary sinus; 2) stabilize the fractured bones in an anatomic reduction for as long as necessary to achieve osteosynthesis; 3) not utilize any foreign bodies; 4) not damage sinus mucosa and maintain normal sinus physiology; 5) provide uncomplicated post operative care; and 6) require only one operation to implant.

The retrievable endoscopic orbital floor splint 10, 100, and 120 of the invention and its use in repairing blowout fractures of the orbital floor involves a retrievable silicone rubber splint that is put into place utilizing an approach through the maxillary sinus. The maxillary sinus may be opened directly, or endoscopic instruments may be employed.

In the case of the first embodiments of FIGS. 1–8, the ring-shaped portion 18 is placed along the medial wall of the maxillary sinus (the widest dimension of the sinus), and is stabilized by the recesses that are formed by the junction of the anterior wall of the maxillary sinus with the medial wall of the maxillary sinus, and the posterior wall of the maxillary sinus with the medial wall of the maxillary sinus. When properly sized (i.e. pediatric and small, medium, and large adult sizes) and located, the ring-shaped portion 18 will be slightly compressed. The deformation in the ring portion will provide the potential kinetic energy necessary the prevent the intraorbital contents from herniating into the sinus.

The double tube design will assure that the ring does not bend in an "S" shaped pattern. Since the side by side tubes will support each other, side to side bends will be eliminated and the ring will only deform in a central direction. This will help prevent displacement and maintain the rings position against the medial antral wall (in the case of the first embodiment of FIGS. 1–8, and generally under pedicle portion 104 in the case the second embodiment of FIG. 9. The ring may or may not be have a neck and may not be angled in that portion of the ring that attaches to the pedicle portion of the implant. The neck has several functions. First, the neck and its angle will allow the maximum energy from the ring to be directed at the middle and mid-medial portions of the orbital floor. These require the most support because they are the weakest portion of the orbital floor and therefore most frequently fractured. Second, the angled portion of the ring will also assure that the ring remains in place against the medial wall of the sinus. Thirdly, the angled will provide a degree of flexibility between the ring and pedicle to assure that pedicle adapts to any irregularities in the angulation of the sinus roof/orbital floor without losing the lift and shape necessary for anatomic reduction and stabilization of the fractured bones.

The pedicle portion 12, 104 and 122 is an irregular curved shape that mimics the typical irregularly curved shape of the sinus roof/orbital floor. The roughly triangular pedicle is angled from its attachment to the ring in such a manner that it is congruent with the angulation of the sinus roof/orbital floor. The pedicle will cover the entire roof of the sinus/orbital floor and will be thin enough to be flexible in order to adapt to minor irregularities in the contour of the sinus roof yet firm enough to prevent fracture displacement.

The curvature of the pedicle will "cup" the fractured bones into the proper shape necessary for an anatomical reduction. The pedicle may also have holes perforating it, knobs covering it, or both. These various surfaces will function to decrease mucosal contact and provide increased circulation or allow drainage of mucous, serum or blood.

The protrusions or knobs that cover the surface of the implants are designed to minimize the contact area between implant and mucosa. This will minimize pressure necrosis and pathologic changes in the mucosa and allow blood flow in the mucosa that is under the implant. Increased blood flow will also help prevent infection and prevents delayed wound healing. The knobs may cover just the mucosal surface of the ring portion, or they may cover the mucosal surface of the whole implant. The smooth style and the perforated style of the pedicle may be used when a graft is required to close an exceptionally large defect. In such cases, the graft material, such as the bone from the anterior maxilla which was removed to access the sinus, can be sutured to the mucosal surface of the pedicle with resorbable suture material prior to placement, and will fuse with the orbital floor.

The implant is placed into the maxillary sinus via an antrostomy in the anterior maxilla (Caldwell-Luc procedure). The herniated tissues are elevated and the bone fragments are rotated back into position under direct vision. The implant pedicle is then properly aligned to cover the roof of the maxillary sinus. A forced duct test is then performed to be sure there is not any entrapment of the inferior rectus muscle, and the gingival incision is then closed. The implant will be removed either endoscopically or via a minimal antrostomy about 6 weeks later. Since the implant is silicone rubber, it is inert and can be removed simply by grasping it and retrieving it. No dissection or tissue disruption will occur. The retrieval will likely be performed in an office setting with light sedation or even under a local anesthetic.

Alternatively, if the implant is manufactured thin enough and flexible enough, it may be placed endoscopically through either the anterior maxilla or maxillary osmium. The surgeon would first do an endoscopic examination to be sure the degree of fracture and herniation was amenable to this approach. Once this is verified, the implant can be placed into the sinus endoscopically and endoscopic instruments will be used to elevate the herniated tissues. After about six weeks of stabilization, the implant would be removed endoscopically as well.

The implant of the invention is also ideal for the repair of orbital floor fractures associated with fractures of the zygomatic-maxillary complex (cheekbone, or ZMC.) Fractures of the orbital floor and anterior maxilla are sine qua non of ZMC fractures. An incision in the maxillary gingiva is required to place a bone plate on the fractured zygomatic buttress in order to stabilize the ZMC. After stabilizing the ZMC it is quite simple to place the implant of the invention into the sinus via the fracture site in-the maxilla. The remainder of the procedure is unaltered.

The device and its method of use and implantations include the following advantages:

1. A safe surgical approach through the maxillary sinus that involves minimal tissue dissection and/or employs an endoscopic approach.
2. No cutaneous scar is left on the patient.
3. There is anatomical reduction of the in situ bones of the orbital floor.
4. There is no permanent implanted foreign body left behind.
5. After the osteosynthesis, the implant can be easily retrieved.
6. There is maintenance of the normal sinus physiology during bone stabilization.
7. The advantages noted in items 3,4,5 should act to decrease the incidence of infection.
8. The ability to place a graft to fill large defects without an orbital dissection.
9. Finally, there are few if any postoperative responsibilities for the patient.

In summary, the unique characteristics of the device and its use include:

1. A small, flexible design which allows endoscopic placement and retrieval;
2. A knobbed mucosal contact surface which maintains sinus physiology during bone stabilization;
3. A compression ring or leg which maintains continuous upward pressure to keep the fractured bones stabilized;
4. A compression ring or leg maintains the patient's maxillary ostium and maintains sinus physiology during bone stabilization;
5. An angle portion of ring to help prevent dislodgment, to direct continuous forces onto correct portion of pedicle portion, and provides flexibility so that the pedicle portion can readily adapt to irregularities in the orbital floor;
6. An anatomically shaped pedicle portion that "cups" and shapes fragments into an exceptionally good anatomical reduction;
7. An intraantral devise that does not require an extraantral "tail" for retrieval; and
8. The ability to place a graft to repair large defects without an orbital dissection.

The above-described embodiments of the present invention are merely descriptive of its principles and are not to be considered limiting. The scope of the present invention instead shall be determined from the scope of the following claims including their equivalents.

What is claimed is:

1. An endoscopic orbital floor splint for placement in a maxillary sinus for supporting an orbital floor, coprising:

a pedicle portion with a flexible supporting surface adapted to substantially cover an upper orbital floor supporting surface and a lower surface; and a resilient support portion extending below the lower surface of the pedicle portion which is adapted to force the pedicle portion upwardly to support the orbital floor.

2. The endoscopic orbital floor splint of claim 1, wherein the pedicle portion has a generally triangular shape.

3. The endoscopic orbital floor splint of claim 1, wherein the pedicle portion has a generally triangular shape with rounded corners and an inferior optical nerve notch formed on one side thereof.

4. The endoscopic orbital floor splint of claim 1, wherein the pedicle portion is generally concave facing upwardly.

5. The endoscopic orbital floor splint of claim 1, wherein the support portion is generally ring-shaped.

6. The endoscopic orbital floor splint of claim 1, wherein the support portion has a generally ring-shape with a neck portion connecting between an upper region of the ring-shape and a bottom of the pedicle portion.

7. The endoscopic orbital floor splint of claim 6, wherein the neck portion extends outwardly from a plane of the ring-shaped support portion.

8. The endoscopic orbital floor splint of claim 6, wherein the neck portion extends outwardly from a plane of the ring-shaped support portion at an angle of at least 60 degrees.

9. The endoscopic orbital floor splint of claim 1, wherein the support portion has a generally ring-shape with two upper ends merged with two ends of a V-shaped neck portion, and an apex of the V being connected to a bottom of the pedicle portion, the V-shaped neck portion extending outwardly from a plane of the support portion.

10. The endoscopic orbital floor splint of claim 1, wherein the endoscopic orbital floor splint is constructed from bio-compatible material which is flexible and resilient.

11. The endoscopic orbital floor splint of claim 1, wherein the endoscopic orbital floor splint is constructed as a unitary structure.

12. The endoscopic orbital floor splint of claim 1, wherein the support portion has a plurality of protrusions formed thereon.

13. The endoscopic orbital floor splint of claim 1, wherein the support portion comprises a leg which extends from a bottom of the pedicle portion.

14. The endoscopic orbital floor splint of claim 1, wherein the pedicle portion has a generally triangular shape with a top surface and a bottom surface and the support portion comprises a leg which extends laterally from a bottom surface of the pedicle portion.

15. The endoscopic orbital floor splint of claim 14, wherein the leg extends laterally from the bottom surface of the pedicle portion at an angle of between 0° and 90°.

16. An endoscopic orbital floor splint for placement in a maxillary sinus for supporting an orbital floor, comprising:
a pedicle portion with an upper surface and lower, the upper surface being generally concave facing upwardly and having a generally triangular shape; and
a generally ring-shape support portion extending below the lower surface of the pedicle portion which is adapted to force pedicle portion upwardly to support the orbital floor, wherein the endoscopic orbital floor splint is constructed from bio-compatible material which is flexible and resilient.

17. The endoscopic orbital floor splint of claim 16, wherein the generally triangular shaped pedicle portion has rounded corners and an inferior optical nerve notch formed on one side thereof.

18. The endoscopic orbital floor splint of claim 16, wherein the endoscopic orbital floor splint is constructed as a unitary structure.

19. The endoscopic orbital floor splint of claim 16, wherein the support portion has a plurality of protrusions formed thereon.

20. An endoscopic orbital floor splint for placement in a maxillary sinus for supporting an orbital floor, comprising:
a pedicle portion with an upper surface and lower, the upper surface being generally concave facing upwardly and having a generally triangular shape; and
a generally ring-shape support portion with a neck portion connecting between an upper region of the ring-shape and a bottom of the pedicle portion which is adapted to force pedicle portion upwardly to support the orbital floor, the neck portion extending outwardly from a plane of the ring-shaped support portion.

21. The endoscopic orbital floor splint of claim 20, wherein the generally triangular shaped pedicle portion has rounded corners and an inferior optical nerve notch formed on one side thereof.

22. The endoscopic orbital floor splint of claim 20, wherein the endoscopic orbital floor splint is constructed as a unitary structure.

23. The endoscopic orbital floor splint of claim 20, wherein the support portion has a plurality of protrusions formed thereon.

24. An endoscopic orbital floor splint for placement in a maxillary sinus for supporting an orbital floor, comprising:
a pedicle portion with an upper surface and lower, the upper surface being generally concave facing upwardly and having a generally triangular shape; and
a support portion comprises a leg which extends laterally from a bottom surface of the pedicle portion which is adapted to force pedicle portion upwardly to support the orbital floor, wherein the endoscopic orbital floor splint is constructed from bio-compatible material which is flexible and resilient.

25. The endoscopic orbital floor splint of claim 24, wherein the generally triangular shaped pedicle portion has rounded corners and an inferior optical nerve notch formed on one side thereof.

26. The endoscopic orbital floor splint of claim 24, wherein the leg extends laterally from the bottom surface of the pedicle portion at an angle of between 0° and 90°.

27. The endoscopic orbital floor splint of claim 24, wherein the endoscopic orbital floor splint is constructed as a unitary structure.

28. The endoscopic orbital floor splint of claim 24, wherein the support portion has a plurality of protrusions formed thereon.

29. An endoscopic orbital floor splint for placement in a maxillary sinus for supporting an orbital floor, comprising:
a generally triangular shaped pedicle portion with an upper surface and lower surface; and
a support portion extending below the lower surface of the pedicle portion which is adapted to force pedicle portion upwardly to support the orbital floor.

30. An endoscopic orbital floor splint for placement in a maxillary sinus for supporting an orbital floor, comprising:
a flexible pedicle portion with a supporting surface adapted to substantially cover the surface of an orbital floor and conform to the shape of the orbital floor and a lower surface; and
a resilient support portion extending below the lower surface of the pedicle portion which is adapted to resiliently force the pedicle portion upwardly to support the orbital floor.

* * * * *